United States Patent [19]
Giani et al.

[11] Patent Number: 4,841,046
[45] Date of Patent: Jun. 20, 1989

[54] PROCESS FOR THE PREPARATION OF PYRIDOBENZODIAZEPINONE

[75] Inventors: Roberto P. Giani, Locate Triulzi; Ettore Parini, Cologno Monzese; Giancarlo Tonon, Milan; Massimiliano Borsa, Vimodrone, all of Italy

[73] Assignee: Dompe' Farmaceutici S.p.A., Milan, Italy

[21] Appl. No.: 262,787

[22] Filed: Oct. 26, 1988

[30] Foreign Application Priority Data

Oct. 30, 1987 [IT] Italy .................................. 48557 A/87

[51] Int. Cl.$^4$ ............................................. C07D 471/04
[52] U.S. Cl. ..................................... 540/495; 514/220
[58] Field of Search ......................... 540/495; 514/220

[56] References Cited

U.S. PATENT DOCUMENTS 3,316,251  4/1967  Schmidt .............................. 540/495

Primary Examiner—Anton H. Sutto
Assistant Examiner—Miriam Sohn
Attorney, Agent, or Firm—Stevens, Davis, Miller & Mosher

[57] ABSTRACT

The present invention refers to an improved method for the preparation of 6,11-dihydro-5H-pyrido[2,3-b][1,5]benzodiazepin-5-one in which the condensation between 2-chloronicotinic acid and o-phenylenediamine is carried out by refluxing in the presence of a solvent consisting of a cycloalkanol. The end product is in pure state and it may be utilized as such.

2 Claims, No Drawings

PROCESS FOR THE PREPARATION OF PYRIDOBENZODIAZEPINONE

The present invention refers to an improved method for the preparation of a pyridobenzodiazepinone, more specifically 6,11-dihydro-5H-pyrido [2,3-b][1,5]benzodiazepin-5-one. 6,11-Dihydro-5H-pyrido [2,3-b][1,5]benzodiazepin-5-one is encompassed in a class of heterocyclic compounds, many of which possessing pharmacological activity, described in Bull. Soc. Chem. France, 1966, No. 7, page 2316 and it is prepared by condensing under reflux in chlorobenzene, 2-chloronicotinic acid and o-phenylenediamine. From the reaction mixture, adding as precipitation aid ethanol, 6,11-dihydro-5H-pyrido [2,3-b][1,5]benzodiazepin-5-one was separated in a very raw state in the form of a product of greenish yellow color, melting at 280° C., and therefore to obtain a product of sufficient purity it was necessary to undergo several re-crystallizations from suitable solvents. Examples of such solvents are acetic acid, pyridine and dioxane. Using as solvents tetrahydronaphthalene, dichloro- or trichloro-benzene or glycol as described in DE No. 24 24 811 this did not result in improving the quality of the end product, because even making use of these solvents, the so obtained 6,11-dihydro-5H-pyrido [2,3-b][1,5]benzodiazepin-5-one was still very impure. 6,11-Dihydro-5H-pyrido [2,3-b][1,5]benzodiazepin-5-one is the starting material in the preparation of 11-(1-methylpiperidin-4-carbonyl)-6,11-dihydro-5H-pyrido [2,3-b][1,5]benzodiazepin-5-one, a very interesting anti-ulcer compound, which has been described and claimed by the Applicant in U.S. Pat. No. 4,556,653; the carrying out of a process which allows to obtain the starting material 6,11-dihydro-5H-pyrido [2,3-b][1,5]benzodiazepin-5-one in a purer state and in higher yield, represents therefore an aim of great interest. It has been now found, and it constitutes the subject of the present invention, that in the preparation of 6,11-dihydro-5H-pyrido [2,3-b][1,5]benzodiazepin-5-one, when the condensation between 2-chloronicotinic acid and o-phenylenediamine takes place in cycloalkanol such as cyclopentanol or cyclohexanol, the final product is obtained in a high degree of purity (color-yellow, melting point 295°-296° C.) and no further re-crystallizations of the same are necessary. The duration of the reaction of condensation may vary upon the cycloalkanol used, in any case it is comprised in the range of 3-14 hours. The use of the cycloalkanol as solvent in the above mentioned reaction makes it possible to obtain an improved process by which 6,11-dihydro-5H-pyrido [2,3-b][1,5]benzodiazepin-5-one at a very high degree of purity is obtained so that it may be used as such without previous purification. Furthermore by the process of the present invention a considerable improvement has been obtained concerning the total yield of the end product, this yield being at least 80%, while according to the process described in Bull. Soc.Chim.France, 1966,No. 70,page 2316, the partial yield of the raw product, evaluated before the re-crystallization, was 70%. A further advantage of the process of the present invention is represented by the fact that in accordance with it, the use of re-crystallization solvents is no longer required, and therefore, apart from realizing noticeable savings, it is no longer necessary to have at disposal storage facilities suitable for those solvents, neither is it necessary to follow precise rules for their use, nor to have suitable plants for their depuration and re-use. The example which follows is given for the purpose of illustrating the invention without limiting it.

EXAMPLE

6,11-Dihydro-5H-pyrido [2,3-b][1,5]benzodiazepin-5-one

A 100ml flask was charged with 15.7g 2-chloronicotinic acid, 10.8g o-phenylenediamine and 60ml cyclohexanol. The reaction mixture was refluxed for 13 hours and the water which formed, removed by azeotropic distillation. The reaction mixture was then cooled to 60° C. and diluted with 40ml ethanol, stirring for 30 minutes at room temperature. The precipitate which was formed was separated by filtration and washed several times with ethanol. Grams 16.9 of a crystalline yellow product, consisting of 6,11-dihydro-5H-pyrido [2,3-b][1,5]benzodiazepin-5-one, melting at 295°-296° C., were obtained.

What we claim is:

1. A process for the preparation of 6,11-dihydro-5H-pyrido [2,3-b][1,5]benzodiazepin-5-one by the condensation of 2-chloronicotinic acid and o-phenylenediamine, characterized in that the reaction of condensation is carried out at reflux in a solvent selected from the group consisting of cyclopentanol and cyclohexanol.

2. A process for the preparation of 6,11-dihydro-5H-pyrido [2,3-b][1,5]benzodiazepin-5-one by the condensation of 2-chloronicotinic acid and o-phenylenediamine, characterized in that the reaction of condensation is carried out at reflux in cyclohexanol.

* * * * *